United States Patent
Lissoos et al.

(10) Patent No.: US 12,246,064 B2
(45) Date of Patent: Mar. 11, 2025

(54) METHOD OF TREATING CROHN'S DISEASE BY ADMINISTERING A TRIPLE COMBINATION THERAPY OF ANTI-INTEGRIN ANTIBODY, ADALIMUMAB AND METHOTREXATE

(71) Applicants: Millennium Pharmaceuticals, Inc., Cambridge, MA (US); Icahn School of Medicine at Mount Sinai, New York, NY (US)

(72) Inventors: Trevor Warren Lissoos, Deerfield, IL (US); Jean-Frederic Colombel, New York, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 374 days.

(21) Appl. No.: 17/152,585

(22) Filed: Jan. 19, 2021

(65) Prior Publication Data
US 2021/0252141 A1    Aug. 19, 2021

Related U.S. Application Data

(63) Continuation of application No. 16/098,572, filed as application No. PCT/US2017/031089 on May 4, 2017, now Pat. No. 10,918,716.

(60) Provisional application No. 62/331,813, filed on May 4, 2016.

(51) Int. Cl.
| | |
|---|---|
| A61K 39/395 | (2006.01) |
| A61K 31/519 | (2006.01) |
| A61K 31/573 | (2006.01) |
| A61K 31/58 | (2006.01) |
| A61K 38/00 | (2006.01) |
| A61P 1/00 | (2006.01) |
| C07K 16/24 | (2006.01) |
| C07K 16/28 | (2006.01) |
| A61K 39/00 | (2006.01) |

(52) U.S. Cl.
CPC ........ *A61K 39/3955* (2013.01); *A61K 31/519* (2013.01); *A61K 31/573* (2013.01); *A61K 31/58* (2013.01); *A61K 38/00* (2013.01); *A61K 39/395* (2013.01); *A61P 1/00* (2018.01); *C07K 16/241* (2013.01); *C07K 16/2842* (2013.01); *A61K 2039/505* (2013.01); *A61K 2039/54* (2013.01); *A61K 2039/545* (2013.01); *A61K 2300/00* (2013.01); *C07K 2317/24* (2013.01)

(58) Field of Classification Search
CPC .............. A61K 39/3955; A61K 31/519; A61K 31/573; A61K 31/58; A61K 2039/54; A61P 1/00; C07K 16/241; C07K 16/2842
See application file for complete search history.

(56) References Cited

U.S. PATENT DOCUMENTS

| | | |
|---|---|---|
| 7,147,851 B1 | 12/2006 | Ponath et al. |
| 7,402,410 B2 | 7/2008 | Ponath et al. |
| 9,663,579 B2 | 5/2017 | Fox et al. |
| 9,764,033 B2 | 9/2017 | Diluzio et al. |
| 10,004,808 B2 | 6/2018 | Fox et al. |
| 10,040,855 B2 | 8/2018 | Diluzio et al. |
| 10,143,752 B2 | 12/2018 | Fox et al. |
| 10,918,716 B2 | 2/2021 | Lissoos et al. |
| 2019/0231878 A1 | 8/2019 | Brown et al. |
| 2020/0206353 A1 | 7/2020 | Fox et al. |
| 2021/0052733 A1 | 2/2021 | Diluzio et al. |
| 2022/0370617 A1 | 11/2022 | Diluzio et al. |

FOREIGN PATENT DOCUMENTS

| | | |
|---|---|---|
| WO | 199624673 A1 | 8/1996 |
| WO | 199806248 A2 | 2/1998 |
| WO | 2001078779 A2 | 10/2001 |
| WO | 2007061679 A1 | 5/2007 |
| WO | 2012151247 A2 | 11/2012 |
| WO | 2012151248 A2 | 11/2012 |
| WO | 2016086147 A1 | 6/2016 |
| WO | 2016105572 A1 | 6/2016 |

OTHER PUBLICATIONS

Asgharpour A, et al. (2013) Clin Exp Gastroenterol. 6:153-160. (doi: 10.2147/CEG.S35163).*
McDonald JW, et al. (Dec. 12, 2012) Cochrane Database Syst Rev. 12:CD003459. (doi: 10.1002/14651858.CD003459.pub3).*
Colman RJ and Rubin DT (Apr. 2015) Journal of Crohn's and Colitis. 9(4):312-317 (doi:10.1093/ecco-jcc/jjv027; Advanced Access Publication Jan. 23, 2015).*
Singh H, et al. (Jan.-Jun. 2016) J Nat Sci Biol Med. 7(1):4-9. (doi: 10.4103/0976-9668.175016).
Sandborn WJ, et al. (Sep. 2007) Gut:56(9):1232-1239. (doi: 10.1136/gut.2006.106781).
Sandborn WJ, et al. (May 2011) AGA Abstracts.
https://www.rxlist.com/humira-drug.htm#description. Accessed from the Internet Feb. 14, 2020.
Carter MJ, et al. (2004) Gut. 53(Suppl V):v1-v16. (doi.org/10.1136/gut.2004.043372).
International Search Report and Written Opinion dated Aug. 2, 2017 in International (PCT) Application No. PCT/US2017/031089 (15 pages).
Cote-Daigneault, Justin, et al. "Biologics in inflammatory bowel disease: what are the data?" United European Gastroenterology Journal, vol. 3, No. 5, pp. 419-428, Oct. 2015.
Hazelwood, Glen S., et al. "Comparative effectiveness of immunosuppressants and biologics for inducing and maintaining remission in Crohn's disease: a network meta-analysis." Gastroenterology, vol. 148, No. 2, pp. 344-354, Feb. 2015.

(Continued)

*Primary Examiner* — Robert S Landsman
(74) *Attorney, Agent, or Firm* — Womble Bond Dickinson (US) LLP (57) ABSTRACT

The invention features new a method for treating inflammatory bowel disease, including Crohn's Disease (CD) or ulcerative colitis in a human patient, comprising administering to a patient a combination therapy comprising an anti-α4β7 antibody, a TNFα antagonist, and an immunomodulator.

15 Claims, 1 Drawing Sheet
Specification includes a Sequence Listing.

(56) References Cited

OTHER PUBLICATIONS

McLean, Leon P., et al. "Vedolizumab for the treatment of ulcerative colitis and Crohn's disease." Immunotherapy, vol. 4, No. 9, pp. 883-898, Sep. 2012.
Buer et al., Inflammatory Bowel Disease 24(5):997-1004, 2018.
Hirten et al., Am J Gastroenterol, Vedolizumab and Infliximab Combination Therapy in the Treatment of Crohn's Disease, Dec. 2015, 110(12):1737-8. doi: 10.1038/ajg.2015.355.
ClinicalTrials.gov archive, NCT02764762 [online], May 5, 2016 <https://clinicaltrials.gov/ct2/history/NCT02764762?V_1=View#StudyPageTop>.
ClinicalTrials.gov archive, Results from Clinical Trial No. NCT02764762 [online], Nov. 8, 2021 <https://clinicaltrials.gov/ct2/show/results/NCT02764762?term=NCT02764762&draw=2&rank=1>.

\* cited by examiner

METHOD OF TREATING CROHN'S DISEASE BY ADMINISTERING A TRIPLE COMBINATION THERAPY OF ANTI-INTEGRIN ANTIBODY, ADALIMUMAB AND METHOTREXATE

RELATED APPLICATIONS

This application is a continuation of U.S. patent application Ser. No. 16/098,572 filed on Nov. 2, 2018, now U.S. Pat. No. 10,918,716, which is a United States National Phase under 35 U.S.C. § 371 of International Application No. PCTUS2017/031089 filed on May 4, 2017, which claims the benefit of U.S. Provisional Application No. 62/331,813 filed on May 4, 2016. The entire contents of the foregoing application are hereby incorporated by reference.

SEQUENCE LISTING

The instant application contains a Sequence Listing which has been submitted in ASCII format via EFS-Web and is hereby incorporated by reference in its entirety. Said ASCII copy, created on Jan. 5, 2021, is named 1200USC1_SEQ_LISTING.TXT and is 12,733 bytes in size.

BACKGROUND

Inflammatory bowel disease (IBD) is a chronic, relapsing, inflammatory disorder of the gastrointestinal (GI) tract that includes 2 entities, namely ulcerative colitis (UC) and Crohn's disease (CD). In contrast to the diffuse, superficial, continuous inflammation limited to the colon in UC, the inflammation of CD is focal, may be transmural, and can involve any segment of the GI tract from mouth to anus. The prevalence of CD is approximately 150/100,000 of the United States (US) population. The characteristic pathology involves a chronic inflammatory infiltrate consisting of neutrophils and macrophages. Hallmarks of CD include granulomatous inflammation and aphthous ulceration. CD is neither medically or surgically curable at the current time. Untreated CD patients commonly develop structural complications that include stricture and fistula formation, which commonly result in hospitalizations and surgery over time. When examining 306 CD patients from the US, Thia et al. (2010, Gastroenterology 139:1147-55) showed that the cumulative risk of developing CD complications of either stricturing or penetrating disease was 33.7% at 5 years and 50.8% at 20 years after establishment of CD diagnosis. The natural course of the disease can range from an indolent course with prolonged periods of remission to aggressive, incapacitating disease associated with structural bowel wall damage. Certain patients have aggressive CD, which could be defined as having a high relapse rate, development of penetrating disease, need for repeat surgery, or multiple admissions for flares. The pathophysiology of IBD is complex as multiple environmental factors interact with the genotype of an individual to cause expression of disease. Published risk factors for aggressive disease include involvement of the upper GI tract and ileum, penetrating disease, early age at diagnosis, smoking, extensive ulceration of the mucosa, high titers of certain serum antibodies, and mutations of the nucleotide-binding oligomerization domain-containing protein 2 (NOD2) gene. The ability to more readily predict which patients will be at higher risk for complications and target more intensive, early treatment to that group would be invaluable. The Crohn's Disease Personalized Risk and Outcome Prediction Tool (PROSPECT), which incorporates clinical, serological, and genetic variables, has been developed by Siegel et al. (Aliment. Pharmacol. Ther. 2016, 43:262-71; Inflamm. Bowel Dis. 2011, 17:30-38). This tool is used to predict the probability of developing complications related to CD, specifically strictures or internal penetrating disease. The output of the predictive model allows risk stratification of patients from low to medium to high risk of complications within a 3-year period.

Treatment with TNF-antagonist therapy substantially improved the care of patients with CD refractory to corticosteroids, immunomodulators, and mesalamine. In 2010, the SONIC trial demonstrated that combination therapy with the TNF antagonist infliximab and immunomodulator azathioprine further significantly improved treatment efficacy. About 40% of patients, however, will not achieve remission after initiation of a combined TNF antagonist and immunomodulator. Thus, there remains an urgent unmet medical need for a combination therapy that can improve remission rates and modify disease progression, particularly for patients who are at higher risk for CD complications.

SUMMARY OF THE INVENTION

The invention relates to methods of treating patient having inflammatory bowel disease (e.g., Crohn's disease (CD) or ulcerative colitis (UC)) using combination therapies that can improve remission rates and modify disease progression.

In one aspect, the patient is at moderate to high risk of complication from the inflammatory bowel disease. In an embodiment, the patient is a high risk CD patient.

In one aspect, the invention provides a method of treating a patient having Crohn's disease using a triple combination therapy comprising a humanized anti-α4β7 antibody, adalimumab, and an immunomodulator, and the triple combination therapy is administered to the patient according to the following dosing regimen: an initial dose of 300 mg of humanized anti-α4β7 antibody as an intravenous infusion, followed by a second subsequent dose of 300 mg of humanized anti-α4β7 antibody as an intravenous infusion at about two weeks after the initial dose; followed by a third subsequent dose of 300 mg of the humanized anti-α4β7 antibody as an intravenous infusion at about six weeks after the initial dose; an initial dose of 160 mg of adalimumab as a subcutaneous injection, followed by a second subsequent dose of 80 mg of adalimumab as a subcutaneous injection, followed by a third subsequent dose of 40 mg of adalimumab at about four weeks after the initial dose; and an initial dose of 15 mg of immunomodulator orally; wherein the dosing regimen results in endoscopic remission and further wherein the anti-α4β7 antibody comprises an antigen binding region of nonhuman origin and at least a portion of an antibody of human origin, the humanized antibody has binding specificity for the α4β7 complex, and the antigen-binding region comprises the CDRs:
Light chain:
CDR1 SEQ ID NO:7
CDR2 SEQ ID NO:8 and
CDR3 SEQ ID NO:9; and
Heavy chain:
CDR1 SEQ ID NO:4
CDR2 SEQ ID NO:5 and
CDR3 SEQ ID NO:6.
In one embodiment, the humanized anti-α4β7 antibody is administered to the patient over about 30 minutes.

In one embodiment, the humanized anti-α4β7 antibody has a heavy chain variable region sequence of amino acids 20 to 140 of SEQ ID NO:1. In one embodiment, the humanized anti-α4β7 antibody has a light chain variable region sequence of amino acids 20 to 131 of SEQ ID NO:2. In yet another embodiment, the humanized anti-α4β7 antibody has a heavy chain comprising amino acids 20 to 470 of SEQ ID NO:1 and a light chain comprising amino acids 20 to 238 of SEQ ID NO:2. In one embodiment, the humanized anti-α4β7 antibody is vedolizumab.

In one embodiment, the immunomodulator is methotrexate.

In one aspect, the method further comprises administering a subsequent dose of 300 mg of the humanized anti-α4β7 antibody as an intravenous infusion at about eight weeks after the third subsequent dose.

In one aspect, the method further comprises administering a subsequent dose of 108 mg of the humanized anti-α4β7 antibody as subcutaneous injection at about every two, three or four weeks after the third subsequent dose.

In one aspect, concomitant corticosteroid use by the patient is tapered to discontinuation during the triple combination therapy.

In one aspect, the invention provides a method of treating a patient having an inflammatory bowel disease, comprising administering to the patient vedolizumab, adalimumab, and methotrexate according to a triple combination therapy wherein the triple combination therapy comprises administering vedolizumab at a dose of 300 mg at weeks 0, 2, and 6, followed by administration every 8 weeks thereafter; subcutaneously administering a 160 mg dose of adalimumab at week 0, an 80 mg dose of adalimumab at week 2, and a 40 mg dose of adalimumab at week 4 and every two weeks thereafter; and administering methotrexate. In one embodiment, adalimumab is discontinued at week 26. In one embodiment, methotrexate is administered orally. In one embodiment, methotrexate is administered at a dose of 15 mg. In one embodiment, methotrexate is discontinued at week 34. In one embodiment, the inflammatory bowel disease is Crohn's disease. In one embodiment, the inflammatory bowel disease is moderately to severely active Crohn's disease. In one embodiment, the patient is a high risk CD patient. In one embodiment, the patient is selected as a high risk CD patient prior to administration of the triple combination therapy. In one embodiment, the inflammatory bowel disease is ulcerative colitis. In one embodiment the ulcerative colitis is moderately to severely active ulcerative colitis.

In one aspect, the invention provides a method of treating a patient having an inflammatory bowel disease, comprising administering to the patient vedolizumab, infliximab, and methotrexate according to a triple combination therapy. The triple combination therapy can comprise administering vedolizumab at a dose of 300 mg at weeks 0, 2, and 6, followed by administration every 8 weeks thereafter; intravenously administering infliximab at a dose of 5 mg/kg at weeks 0, 2 and 6, and then every eight weeks thereafter; and administering methotrexate. In one embodiment, methotrexate is administered orally. In one embodiment, methotrexate is administered at a dose of 15 mg. In one embodiment, methotrexate is discontinued at week 34. In one embodiment, the inflammatory bowel disease is Crohn's disease. In one embodiment, the inflammatory bowel disease is moderately to severely active Crohn's disease. In one embodiment, the patient is a high risk CD patient. In one embodiment, the patient is selected as a high risk CD patient prior to administration of the triple combination therapy. In one embodiment, the inflammatory bowel disease is ulcerative colitis. In one embodiment, the ulcerative colitis is moderately to severely active ulcerative colitis.

In one aspect, the invention provides a method of treating a patient having an inflammatory bowel disease, comprising administering to the patient vedolizumab, golimumab, and methotrexate according to a triple combination therapy. The triple combination therapy can comprise administering vedolizumab at a dose of 300 mg at weeks 0, 2, and 6, followed by administration every 8 weeks thereafter; subcutaneously administering golimumab at a dose of 200 mg at week 0, 100 mg at week 2, and 100 mg every four weeks thereafter; and administering methotrexate. In one embodiment, methotrexate is administered orally. In one embodiment, methotrexate is administered at a dose of 15 mg. In one embodiment, methotrexate is discontinued at week 34. In one embodiment, the inflammatory bowel disease is Crohn's disease. In one embodiment, the inflammatory bowel disease is moderately to severely active Crohn's disease. In one embodiment, the patient is a high risk CD patient. In one embodiment, the patient is selected as a high risk CD patient prior to administration of the triple combination therapy. In one embodiment, the inflammatory bowel disease is ulcerative colitis. In one embodiment, the ulcerative colitis is moderately to severely active ulcerative colitis.

In one aspect, the invention provides a method of treating a patient having an inflammatory bowel disease, comprising administering to the patient vedolizumab, certolizumab pegol, and methotrexate according to a triple combination therapy. The triple combination therapy can comprise administering vedolizumab at a dose of 300 mg at weeks 0, 2, and 6, followed by administration every 8 weeks thereafter; subcutaneously administering certolizumab at a dose of 400 mg at week 0, 400 mg at weeks 2 and 4, and optionally 400 mg every four weeks thereafter; and administering methotrexate. In one embodiment, methotrexate is administered orally. In one embodiment, methotrexate is administered at a dose of 15 mg. In one embodiment, methotrexate is discontinued at week 34. In one embodiment, the inflammatory bowel disease is Crohn's disease. In one embodiment, the inflammatory bowel disease is moderately to severely active Crohn's disease. In one embodiment, the patient is a high risk CD patient. In one embodiment, the patient is selected as a high risk CD patient prior to administration of the triple combination therapy. In one embodiment, the inflammatory bowel disease is ulcerative colitis. In one embodiment, the ulcerative colitis is moderately to severely active ulcerative colitis.

DETAILED DESCRIPTION

Figure 1:
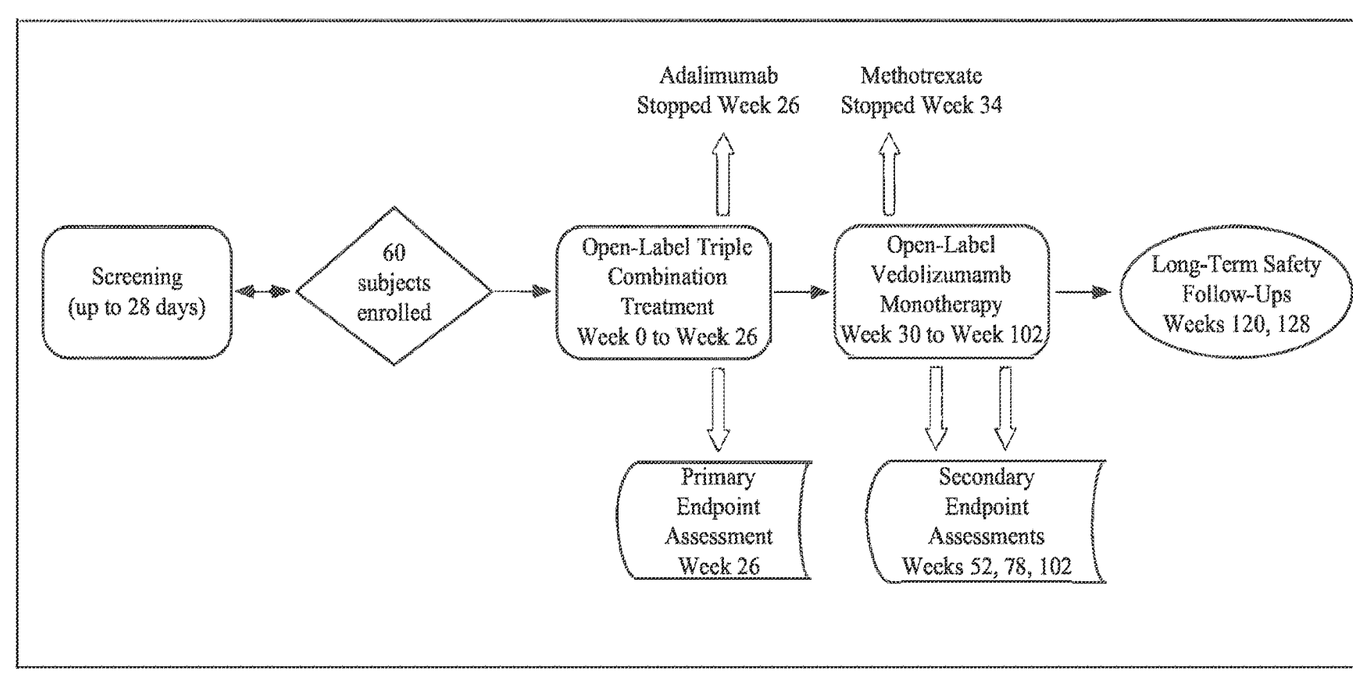
FIG. 1 is a schematic illustrating an overview of the study design.

The present invention relates to a method of treating inflammatory bowel disease (e.g., Crohn's Disease or ulcerative colitis) with a triple combination therapy. The method comprises administering a triple combination therapy, comprising an anti-integrin α4β7 (e.g., vedolizumab), a TNFα antagonist (e.g., adalimumab), and an immunomodulator (e.g., methotrexate), to a patient with Crohn's Disease, particularly a patient at high risk for developing complications.

In one aspect, the patient is administered the triple combination therapy through one or more administration routes.

In some embodiments, the anti-integrin is administered as an infusion, the TNF antagonist as a subcutaneous injection, and the immunomodulator orally.

In some embodiments, the anti-integrin component of the triple combination therapy is an antibody, such as an anti-α4β7 antibody. In some embodiments, the anti-α4β7 antibody is a humanized antibody, e.g., a humanized antibody with the epitopic specificity of Act-1 mouse monoclonal antibody. In some embodiments, the anti-α4β7 antibody is vedolizumab.

In some embodiments, the TNF antagonist is adalimumab. In some embodiments, the TNF antagonist is infliximab, golimumab, or certolizumab pegol.

In some embodiments, the immunomodulator is methotrexate. In some embodiments, the immunomodulator is azathioprine or 6-mercaptopurine.

Definitions

The term "combination therapy", as used herein, refers to the administration of two or more therapeutic substances, e.g., an anti-α4β7 antibody and another drug. The other drug(s) may be administered concomitant with, prior to, or following the administration of an anti-α4β7 antibody. The term "triple combination therapy" as used herein, refers to the administration of at least three therapeutic substances, e.g., an anti-α4β7 antibody, an anti-TNF antibody, and methotrexate.

The terms "TNFα antagonist" or "TNF antagonist", as used interchangeably herein, refer to a therapeutic agent that inhibits, antagonizes, and/or neutralizes TNFα activity. Examples of a TNF antagonist include, but are not limited to, adalimumab, infliximab, golimumab, certolizumab pegol, and etanercept.

The term "high risk Crohn's Disease (CD) patient" refers to a patient having Crohn's Disease who has at least a 20% chance of a disease complication by year 2 following diagnosis as determined by the Crohn's Disease Personalized Risk and Outcome Prediction Tool (PROSPECT) predictive tool (Siegel, et al., *Aliment. Pharmacol. Ther.* 2016; 43:262-271). In one embodiment, the methods disclosed herein are used to treat a patient in this particular subpopulation.

Alternatively, the term "high risk Crohn's Disease (CD) patient" refers to a patient having Crohn's Disease who has a risk of complications as defined by the 2014 American Gastroenterological Association (AGA) CD Clinical Care Pathway Criteria (Sandborn, *Gastroenterology* 2014, 147: 702-705). The criteria assess the severity of the current and prior disease burden, such as initial diagnosis <30 years of age, extensive anatomic involvement, perianal and/or severe rectal disease, deep ulcers, prior surgical resection or stricturing and/or penetrating behavior. In one embodiment, the methods disclosed herein are used to treat a patient whose CD has at least one of these criteria. In one embodiment, the methods disclosed herein are not used to treat a patient who has had prior surgical resection.

"Baseline" as used herein describes a value of a parameter which is measured prior to the initial dose of a treatment. It can refer to a measurement of a sample obtained the same day, the day before, during the week before initial treatment, i.e., at a time period before the first dose when little change is expected until after the first dose and values of the measurement obtained after the first dose can be compared to this baseline value to represent the change caused by the dose.

The term "pharmaceutical formulation" refers to a preparation that contains an α4β7 antagonist, such as an anti-α4β7 antibody, in such form as to permit the biological activity of the antibody to be effective, and which contains no additional components which are unacceptably toxic to a subject to which the formulation would be administered.

The cell surface molecule, "α4β7 integrin," or "α4β7," is a heterodimer of an $\alpha_4$ chain (CD49D, ITGA4) and a $\beta_7$ chain (ITGB7). Each chain can form a heterodimer with an alternative integrin chain, to form $\alpha_4\beta_1$ or $\alpha_E\beta_7$. Human $\alpha_4$ and $\beta_7$ genes (GenBank (National Center for Biotechnology Information, Bethesda, Md.) RefSeq Accession numbers NM_000885 and NM_000889, respectively) are expressed by B and T lymphocytes, particularly memory CD4+ lymphocytes. Typical of many integrins, α4β7 can exist in either a resting or activated state. Ligands for α4β7 include vascular cell adhesion molecule (VCAM), fibronectin and mucosal addressin (MAdCAM (e.g., MAdCAM-1)).

An "α4β7 antagonist" is a molecule which antagonizes, reduces or inhibits the function of α4β7 integrin. Such antagonist may antagonize the interaction of α4β7 integrin with one or more of its ligands. An α4β7 antagonist may bind either chain of the heterodimer or a complex requiring both chains of the α4β7 integrin, or it may bind a ligand, such as MAdCAM. An α4β7 antagonist may be an antibody which performs such binding function, such as an anti-α4β7-integrin antibody or "anti-α4β7 antibody". In some embodiments, an α4β7 antagonist, such as an anti-α4β7 antibody, has "binding specificity for the α4β7 complex" and binds to α4β7, but not to α4β1 or αEβ7.

The term "antibody" or "antibodies" herein is used in the broadest sense and specifically covers full length antibody, antibody peptide(s) or immunoglobulin(s), monoclonal antibodies, chimeric antibodies (including primatized antibodies), polyclonal antibodies, human antibodies, humanized antibodies and antibodies from non-human species, including human antibodies derived from a human germline immunoglobulin sequence transduced into the non-human species, e.g., mouse, sheep, chicken or goat, recombinant antigen binding forms such as monobodies and diabodies, multispecific antibodies (e.g. bispecific antibodies) formed from at least two full length antibodies (e.g., each portion comprising the antigen binding region of an antibody to a different antigen or epitope), and individual antigen binding fragments of any of the foregoing, e.g., of an antibody or the antibody from which it is derived, including dAbs, Fv, scFv, Fab, F(ab)'₂, Fab'.

The term "monoclonal antibody" as used herein refers to an antibody obtained from a population of substantially homogeneous antibodies, i.e., the individual antibodies comprising the population are identical and/or bind the same epitope. The modifier "monoclonal" indicates the character of the antibody as being obtained from a substantially homogeneous population of antibodies, and is not to be construed as requiring production of the antibody by any particular method.

"Antigen binding fragments" of an antibody preferably comprise at least the variable regions of the heavy and/or light chains of an anti-α4β7 antibody. For example, an antigen binding fragment of vedolizumab can comprise amino acid residues 20-131 of the humanized light chain sequence of SEQ ID NO:2 and amino acid residues 20-140 of the humanized heavy chain sequence of SEQ ID NO:1. Examples of such antigen binding fragments include Fab fragments, Fab' fragments, Fv fragments, scFv and F(ab')₂ fragments. Antigen binding fragments of an antibody can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the CH$_f$ domain and hinge region of the heavy chain. In one aspect, antigen binding fragments inhibit binding of α4β7 integrin to one or more of its ligands (e.g. the mucosal addressin MAdCAM (e.g., MAdCAM-1), fibronectin).

A "therapeutic monoclonal antibody" is an antibody used for therapy of a human subject. Therapeutic monoclonal antibodies disclosed herein include anti-α4β7 antibodies.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), and the like. To assess ADCC activity of a molecule of interest, an in vitro ADCC assay, such as those described in U.S. Pat. No. 5,500,362 or 5,821,337 may be performed.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of antibodies are well known.

The "light chains" of antibodies from any vertebrate species can be assigned to one of two clearly distinct types, called kappa (κ) and lambda (λ), based on the amino acid sequences of their constant domains.

The term "hypervariable region" when used herein refers to the amino acid residues of an antibody which are responsible for antigen binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human antibody are replaced by corresponding non-human residues. Furthermore, humanized antibodies may comprise residues that are not found in the recipient antibody or in the donor antibody. These modifications are made to further refine antibody performance. For further details, see Jones et al., *Nature* 321:522-525 (1986); Riechmann et al., *Nature* 332:323-329 (1988); and Presta, *Curr. Op. Struct. Biol.* 2:593-596 (1992).

An "affinity matured" antibody has one or more alterations in one or more hypervariable regions thereof which result an improvement in the affinity of the antibody for antigen, compared to a parent antibody which does not possess those alteration(s). In one aspect, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

An "isolated" antibody is one which has been identified and separated and/or recovered from a component of its natural environment. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

"Treatment" refers to therapeutic treatment. Those in need of treatment include those already with disease. Hence, the patient, e.g., human, to be treated herein may have been diagnosed as suffering from a disease, such as an inflammatory bowel disease, e.g., Crohn's Disease or ulcerative colitis. The terms "patient" and "subject" are used interchangeably herein.

"Prevention" refers to a treatment that results in the absence or reduction in the severity of an adverse event. In a population of patients, when treatment typically results in a certain percentage of adverse events, or a certain percentage of adverse events that are severe, but a treatment administered for prevention purposes instead results in a lower percentage of adverse events (i.e., a lower or reduced risk of adverse events) or a lower percentage of adverse events that are severe (i.e., a lower or reduced risk that the adverse event is severe).

An anti-α4β7 antibody, vedolizumab, a humanized monoclonal antibody that has binding specificity for the α$_4$β$_7$ integrin, is already indicated for the treatment of patients with moderately to severely active ulcerative colitis (UC) and Crohn's disease (CD). Vedolizumab has a novel gut-selective mechanism of action. By binding to cell surface-expressed α$_4$β$_7$, vedolizumab is an α4β7 antagonist and blocks a subset of memory gut-homing T lymphocytes from interacting with mucosal addressin cell adhesion molecule-1 (MAdCAM-1) expressed on endothelial cells.

Several factors are associated with accelerated clearance of antibodies including the presence of anti-drug antibodies, sex, body size, concomitant immunosuppressant use, disease type, albumin concentration, and degree of systemic inflammation. Furthermore, a consistent relationship between efficacy and exposure, in distinction to drug dose, has been observed for many of these agents, such that higher trough drug concentrations are associated with greater efficacy. Differences in drug clearance may be an important explanation for this observation. For example, cancer patients undergo immunosuppressive treatment of the tumor and treatment for infection. Therefore, an understanding of the determinants of clearance for therapeutic antibodies in transplant patients may result in optimization of drug regimens.

In previous studies, single-dose pharmacokinetics, pharmacodynamics ($\alpha_4\beta_7$ receptor saturation), safety, and tolerability of vedolizumab were investigated over a dose range of 0.2 to 10 mg/kg in healthy volunteers (intravenous [IV] infusion) (unpublished data). After reaching peak concentrations, vedolizumab serum concentrations fell in a generally biexponential fashion until concentrations reached approximately 1 to 10 ng/mL. Thereafter, concentrations appeared to fall in a nonlinear fashion. The multiple-dose pharmacokinetics and pharmacodynamics of vedolizumab have been investigated following IV infusions of 0.5 and 2 mg/kg in patients with CD and infusion of 2, 6, and 10 mg/kg in patients with UC. Vedolizumab pharmacokinetics was generally linear following an IV infusion over the dose range of 2 to 10 mg/kg in patients with UC. After multiple-dose administration, rapid and near complete $\alpha_4\beta_7$ receptor saturation was achieved following the initial dose of vedolizumab.

The efficacy and safety of vedolizumab induction and maintenance therapy were demonstrated in patients with CD in the GEMINI 2 (ClinicalTrials.gov number, NCT00783692) and GEMINI 3 (ClinicalTrials.gov number, NCT01224171) trials. The exposure-response (efficacy) relationships of vedolizumab in patients with CD for induction and maintenance therapy have been presented elsewhere.

The TNF antagonist may be Adalimumab. Adalimumab is a recombinant human IgG1 monoclonal antibody specific for human TNF-$\alpha$. Adalimumab binds specifically to TNF-$\alpha$ and blocks its interaction with the p55 and p75 cell surface TNF-$\alpha$ receptors. Adalimumab also lyses surface TNF-$\alpha$ expressing cells in vitro in the presence of complement. Adalimumab does not bind or inactivate lymphotoxin (TNF-$\beta$). TNF-$\alpha$ is a naturally occurring cytokine that is involved in normal inflammatory and immune responses. TNF-$\alpha$ plays an important role in both the pathologic inflammation and the joint destruction that are hallmarks of inflammatory disease. Adalimumab also modulates biological responses that are induced or regulated by TNF-$\alpha$, including changes in the levels of adhesion molecules responsible for leukocyte migration.

Adalimumab is approved globally for the treatment of moderately to severely active CD in patients who have had an inadequate response to conventional therapy. Additionally, adalimumab is approved for reducing signs and symptoms and inducing clinical remission in these patients if they have also lost response to or are intolerant to infliximab.

Adalimumab 40 mg weekly or every other week has been shown to be effective for maintaining clinical remission in patients with CD who have responded to adalimumab induction therapy. Adalimumab has also been shown to have corticosteroid-sparing effects in patients with CD (Behm B W BS. Cochrane Database of Systematic Reviews 2008(1)).

The immunomodulator may be an antimetabolite. Methotrexate is an antimetabolite that is approved for the treatment of certain neoplastic diseases, severe psoriasis, and adult rheumatoid arthritis. Methotrexate was originally developed as an antineoplastic, and is an inhibitor of the enzyme dihydrofolate reductase, which catalyzes a reaction in the production of tetrahydrofolic acid. This pathway is essential to the synthesis of the purine and pyrimidine components of deoxyribonucleic acid (DNA), and thus the drug slows cellular division. Although the mechanism of action of low-dose methotrexate in the treatment of autoimmune disease is not well understood, there is evidence supporting both immunosuppressive and anti-inflammatory effects.

Treatment of Inflammatory Bowel Disease with Triple Combination Therapy

The invention relates to a method of treating inflammatory bowel disease (e.g., Crohn's Disease (CD) or ulcerative colitis) in a patient using a triple combination therapy. The human patient may be an adult (e.g., 18 years or older), an adolescent, or a child. The triple combination therapy may improve remission rates and modify disease progression by including agents with different mechanisms of action, particularly for patients who are at higher risk for CD complications. Patients who respond to treatment with infliximab or adalimumab have been shown to have a decrease in MAdCAM and an increase in $\alpha 4\beta 7$-positive cells (Biancheri P, et al. Inflamm Bowel Dis 2013; 19(2):259-64.). Thus, their vedolizumab pathway is active, and the addition of vedolizumab to the therapy regimen can provide clinically relevant synergy.

In one embodiment, the triple combination therapy of the invention is used to treat patients who are at high risk for developing complications from inflammatory bowel disease. For example, patients at high risk for developing complications from CD, or aggressive CD, may include those patients with involvement of the upper GI tract and ileum, penetrating disease, early age at diagnosis, smoking, extensive ulceration of the mucosa, high titers of serum antibodies, use of corticosteroids at diagnosis, and mutations of the NOD2 gene. Patients at high risk for developing complications of CD may be defined as described above for the PROSPECT algorithm or the AGA criteria. Patients identified as high risk CD patients can be targeted for triple combination therapy. The patient targeted for triple combination therapy may have a Simple Endoscopic Score for Crohn's Disease (SES-CD) of ≥7 or ≥4 if isolated ileal disease. The patient targeted for triple combination therapy may have active disease as judged by the Crohn's Disease Activity Index (CDAI) of ≥220. The CDAI score weighs factors including the number of liquid or very soft stools, the severity of abdominal pain, general well being, extra-intestinal manifestations of the disease, such as arthritis, iritis, erythemia, fistula or abscess or fever, whether the patient is taking an antidiarrheal medication, abdominal mass, hematocrit and body weight.

Anti-Integrin

An anti-integrin, such as an anti-$\alpha 4\beta 7$ antibody, is administered in an effective amount which inhibits binding of $\alpha 4\beta 7$ integrin to a ligand thereof. For therapy, an effective amount will be sufficient to achieve the desired effect (e.g., inducing endoscopic remission, inducing mucosal healing, achieving clinical remission, achieving biomarker remission). An $\alpha 4\beta 7$ antagonist, such as an anti-$\alpha 4\beta 7$ antibody may be administered in a unit dose or multiple doses. The dosage can be determined by methods known in the art and can be dependent, for example, upon the individual's age, sensitivity, tolerance and overall well-being. Examples of modes of administration include topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for antibodies can be from about 0.1 mg/kg body weight to about 10.0 mg/kg body weight per treatment, for example about 2 mg/kg to about 7 mg/kg, about 3 mg/kg to about 6 mg/kg, or about 3.5 to about 5 mg/kg. In particular embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. In some embodiments, vedolizumab is administered at a dose of 50 mg, 75 mg, 100 mg, 300 mg, 450 mg, 500 mg or 600 mg. In some embodiments, vedolizumab is administered at a dose of 108 mg, 90 to 120 mg, 216 mg, 160 mg, 165 mg, 155 to 180 mg, 170 mg or 180 mg. In some embodiments, the anti-α4β7 antibody, such as vedolizumab is provided as a dry, lyophilized formulation which can be reconstituted with a liquid, such as sterile water, for administration. Administration of a reconstituted formulation can be by parenteral injection by one of the routes described above. An intravenous injection can be by infusion, such as by further dilution with sterile isotonic saline, buffer, e.g., phosphate-buffered saline or Ringer's (lactated or dextrose) solution. In some embodiments, the anti-α4β7 antibody is administered by subcutaneous injection, e.g., a dose of about 108 mg or about 165 mg or about 216 mg, at about every two, three or four weeks after the start of therapy or after the third subsequent dose.

The anti-integrin, which is an anti-α4β7 antibody, can bind to an epitope on the α4 chain (e.g., humanized MAb 21.6 (Bendig et al., U.S. Pat. No. 5,840,299), on the β7 chain (e.g., FIB504 or a humanized derivative (e.g., Fong et al., U.S. Pat. No. 7,528,236)), or to a combinatorial epitope formed by the association of the α4 chain with the β7 chain. AMG-181 or other antibodies described in US 2010/0254975 are anti-α4β7 antibodies. In one aspect, the antibody binds a combinatorial epitope on the α4β7 complex, but does not bind an epitope on the α4 chain or the β7 chain unless the chains are in association with each other. The association of α4 integrin with β7 integrin can create a combinatorial epitope for example, by bringing into proximity residues present on both chains which together comprise the epitope or by conformationally exposing on one chain, e.g., the α4 integrin chain or the β7 integrin chain, an epitopic binding site that is inaccessible to antibody binding in the absence of the proper integrin partner or in the absence of integrin activation. In another aspect, the anti-α4β7 antibody binds both the α4 integrin chain and the β7 integrin chain, and thus, is specific for the α4β7 integrin complex. Such antibodies can bind α4β7 but not bind α4β1, and/or not bind $\alpha_E$β7, for example. In another aspect, the anti-α4β7 antibody binds to the same or substantially the same epitope as the Act-1 antibody (Lazarovits, A. I. et al., *J. Immunol.*, 133(4): 1857-1862 (1984), Schweighoffer et al., *J. Immunol.*, 151(2): 717-729, 1993; Bednarczyk et al., *J. Biol. Chem.*, 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf Millennium Pharmaceuticals, Inc., 40 Landsdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the anti-integrin is an anti-MAdCAM antibody (see e.g., U.S. Pat. No. 8,277,808, PF-00547659 or antibodies described in WO2005/067620), or an engineered form of a ligand, such as a MAdCAM-Fc chimera such as described in U.S. Pat. No. 7,803,904.

In one aspect, the anti-integrin inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs are described in the PCT publication WO 96/24673, the entire teachings of which are incorporated herein by this reference. In another aspect, the anti-integrin inhibits binding of α4β7 to MAdCAM (e.g., MAdCAM-1) and/or fibronectin without inhibiting the binding of VCAM.

In one aspect, the anti-integrin, e.g., an anti-α4β7 antibody, has the binding specificity, e.g., comprises the complementarity determining regions of mouse Act-1 antibody. For example, an anti-α4β7 antibody comprises a heavy chain that contains the 3 heavy chain complementarity determining regions (CDRs, CDR1, SEQ ID NO:4, CDR2, SEQ ID NO:5 and CDR3, SEQ ID NO:6) of the mouse Act-1 antibody and suitable human heavy chain framework regions; and also comprises a light chain that contains the 3 light chain CDRs (CDR1, SEQ ID NO:7, CDR2, SEQ ID NO:8 and CDR3, SEQ ID NO:9) of the mouse Act-1 antibody and suitable human light chain framework regions. In some embodiments the anti-α4β7 antibody is an IgG1 isotype.

In one aspect, the anti-integrin for use in the treatments are humanized versions of the mouse Act-1 antibody. Suitable methods for preparing humanized antibodies are well-known in the art. Generally, the humanized anti-α4β7 antibody will contain a heavy chain that contains the 3 heavy chain complementarity determining regions (CDRs, CDR1, SEQ ID NO:4, CDR2, SEQ ID NO:5 and CDR3, SEQ ID NO:6) of the mouse Act-1 antibody and suitable human heavy chain framework regions; and also contain a light chain that contains the 3 light chain CDRs (CDR1, SEQ ID NO:7, CDR2, SEQ ID NO:8 and CDR3, SEQ ID NO:9) of the mouse Act-1 antibody and suitable human light chain framework regions. The humanized Act-1 antibody can contain any suitable human framework regions, including consensus framework regions, with or without amino acid substitutions. For example, one or more of the framework amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference. Treatment methods using anti-α4β7 integrin antibodies are described in publication nos. U.S. 2005/0095238, U.S. 2005/0095238, WO2012151248 and WO 2012/151247.

In one aspect, the anti-integrin is the anti-α4β7 antibody, vedolizumab. Vedolizumab IV (also called MLN0002, ENTYVIO™ or KYNTELES™) is a humanized antibody (Ig) G1 mAb directed against the human lymphocyte integrin α4β7. The α4β7 integrin mediates lymphocyte trafficking to GI mucosa, gut-associated lymphoid tissue (GALT) and mesenteric lymph nodes through adhesive interaction with mucosal addressin cell adhesion molecule-1 (MAdCAM-1), which is expressed on the endothelium of mesenteric lymph nodes and GI mucosa. Vedolizumab binds the α4β7 integrin, antagonizes its adherence to MAdCAM-1 and as such, impairs the migration of naïve T cells to the GALT and mesenteric lymph nodes and gut homing leukocytes into GI mucosa.

In another aspect, the anti-integrin is a humanized anti-α4β7 antibody for use in the treatment and comprises a heavy chain variable region comprising amino acids 20 to 140 of SEQ ID NO:1, and a light chain variable region comprising amino acids 20 to 131 of SEQ ID NO:2 or amino acids 1 to 112 of SEQ ID NO:3. If desired, a suitable human constant region(s) can be present. For example, the humanized anti-α4β7 antibody can comprise a heavy chain that comprises amino acids 20 to 470 of SEQ ID NO:1 and a light chain comprising amino acids 1 to 219 of SEQ ID NO:3. In another example, the humanized anti-α4β7 antibody can comprise a heavy chain that comprises amino acids 20 to 470 of SEQ ID NO:1 and a light chain comprising amino acids 20 to 238 of SEQ ID NO:2. Vedolizumab is cataloged under Chemical Abstract Service (CAS, American Chemical Society) Registry number 943609-66-3).

Substitutions to the humanized anti-α4β7 antibody sequence can be, for example, mutations to the heavy and light chain framework regions, such as a mutation of isoleucine to valine on residue 2 of SEQ ID NO:10; a mutation of methionine to valine on residue 4 of SEQ ID NO:10; a mutation of alanine to glycine on residue 24 of SEQ ID NO:11; a mutation of arginine to lysine at residue 38 of SEQ ID NO:11; a mutation of alanine to arginine at residue 40 of SEQ ID NO:11; a mutation of methionine to isoleucine on residue 48 of SEQ ID NO:11; a mutation of isoleucine to leucine on residue 69 of SEQ ID NO:11; a mutation of arginine to valine on residue 71 of SEQ ID NO:11; a mutation of threonine to isoleucine on residue 73 of SEQ ID NO:11; or any combination thereof; and replacement of the heavy chain CDRs with the CDRs (CDR1, SEQ ID NO:4, CDR2, SEQ ID NO:5 and CDR3, SEQ ID NO:6) of the mouse Act-1 antibody; and replacement of the light chain CDRs with the light chain CDRs (CDR1, SEQ ID NO:7, CDR2, SEQ ID NO:8 and CDR3, SEQ ID NO:9) of the mouse Act-1 antibody.

The dose can be administered to the patient over about 20 minutes, about 25 minutes, about 30 minutes, about 35 minutes, or about 40 minutes. In some embodiments, the dose can be administered to the patient for up to two hours.

TNF Antagonist

The invention features a triple combination therapy which includes administration of a TNF antagonist for the treatment of an inflammatory bowel disease. A TNF antagonist is administered in an effective amount which inhibits binding TNF-α and blocks its interaction with the p55 and p75 cell surface TNF-α receptors. Suitable TNF antagonists include, for example, adalimumab, infliximab, etanercept, golimumab, certolizumab pegol, biosimilars thereof and equivalents thereof. For therapy, an effective amount will be sufficient to achieve the desired effect (e.g., inducing endoscopic remission, inducing mucosal healing, achieving clinical remission, achieving biomarker remission). A TNF antagonist, such as an anti-TNF-α antibody (e.g., adalimumab) may be administered in a unit dose or multiple doses. The dosage can be determined by methods known in the art and can be dependent, for example, upon the individual's age, sensitivity, tolerance and overall well-being. Examples of modes of administration include topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for antibodies can be from about 0.1 mg/kg body weight to about 10.0 mg/kg body weight per treatment, for example about 1 mg/kg to about 8 mg/kg, about 2 mg/kg to about 7 mg/kg, about 3 mg/kg to about 6 mg/kg, or about 3.5 to about 5 mg/kg. In particular embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. In some embodiments, the TNF antagonist is administered at a dose of 40 mg, 50 mg, 75 mg, 80 mg, 100 mg, 150 mg, 160 mg, 175 mg, 200 mg, 300 mg, 400 mg, 450 mg, 500 mg or 600 mg. In some embodiments, the TNF antagonist is administered at a dose of 40 mg, 80 mg, 160 mg, 80 to 200 mg, 170 mg, 165 mg, 155 mg, 150 to 180 mg, 140 mg or 130 mg.

In one embodiment, the triple combination therapy of the invention includes the use of adalimumab for the treatment of an inflammatory bowel disease. Adalimumab may be administered to a patient having an inflammatory bowel disease, such as Crohn's disease or ulcerative colitis. In one embodiment, adalimumab is subcutaneously administered to a subject having Crohn's disease or ulcerative colitis at an initial dose of 160 mg at week 0, followed by a second dose of 80 mg at week 2, followed by a 40 dose at week 4 and every two weeks thereafter. In one embodiment, the triple combination therapy comprises discontinuing adalimumab at week 26 of treatment in the patient.

In one embodiment, the triple combination therapy of the invention includes the use of infliximab for the treatment of an inflammatory bowel disease, such as Crohn's disease or ulcerative colitis. In one embodiment, infliximab is intravenously administered to a subject having Crohn's disease or ulcerative colitis at a dose of 5 mg/kg at weeks 0, 2 and 6 weeks, and then every 8 weeks thereafter. In one embodiment, the triple combination therapy comprises discontinuing infliximab at week 26 of treatment in the patient.

In one embodiment, the triple combination therapy of the invention includes the use of golimumab for the treatment of an inflammatory bowel disease, such as Crohn's disease or ulcerative colitis. In one embodiment, golimumab is subcutaneously administered to a subject having Crohn's disease or ulcerative colitis at a dose of 200 mg at week 0, followed by a 100 mg dose a week 2, followed by a 100 mg dose every 4 weeks thereafter. In one embodiment, the triple combination therapy comprises discontinuing golimumab at week 26 of treatment in the patient.

In one embodiment, the triple combination therapy of the invention includes the use of certolizumab pegol for the treatment of an inflammatory bowel disease, such as Crohn's disease or ulcerative colitis. In one embodiment, certolizumab pegol is subcutaneously administered to a subject having Crohn's disease or ulcerative colitis at a dose of 400 mg at week 0, followed by 400 mg doses at weeks 2 and 4. If a response occurs, then 400 mg of certolizumab pegol is administered every four weeks thereafter. In one embodiment, the triple combination therapy comprises discontinuing certolizumab pegol at week 26 of treatment in the patient.

Immunomodulators

An immunomodulator is administered in an effective amount to reduce immunogenicity. Examples of suitable immunomodulators include fluorouracil, cladribine, capecitabline, methotrexate, pemetrexed, mercaptopurine, hydroxyurea, gemcitabine, fludarabine, pralatrexate, clofarabine, cytarabine, decitabine, floxuridine, nelarabine, and thioguanine. In one embodiment the immunomodulator is methotrexate. For therapy, an effective amount will be sufficient to achieve the desired effect (e.g., inducing endoscopic remission, inducing mucosal healing, achieving clinical remission, achieving biomarker remission). An immunomodulator, such as an antimetabolite (e.g., methotrexate) may be administered in a unit dose or multiple doses. The dosage can be determined by methods known in the art and can be dependent, for example, upon the individual's age, sensitivity, tolerance and overall well-being. Examples of modes of administration include oral administration, topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for immunomodulators can be a dose of 5 mg, 10 mg, 15 mg, 20 mg, 25 mg, 30 mg, or 45 mg. In some embodiments, methotrexate is administered at a dose of 10 mg, 15 mg, 20 mg, 10 to 30 mg, 25 mg, 30 mg, or 45 mg.

The dose of the immunomodulator, e.g., methotrexate, can be administered to the patient daily, weekly, or monthly. In some embodiments, the dose can be administered to the patient orally weekly for up to 34 weeks.

The triple combination therapy, such as anti-integrin/TNF antagonist/immunomodulator, may be administered to an individual (e.g., a human) in series, in parallel, or simultaneously. The triple combination therapy may be administered to an individual by a single route of administration, by two different routes of administration, or by three different routes of administration.

In one embodiment, the dosing regimen comprises administration of 300 mg of the anti-integrin by intravenous infusion at Weeks 0, 2, 6, and then every 8 weeks thereafter; administration of 160 mg of the TNF antagonist, e.g., adalimumab, by subcutaneous injection at Week 0, administration of 80 mg of the TNF antagonist, e.g., adalimumab, at Week 2, and then 40 mg of the TNF antagonist, e.g., adalimumab, every 2 weeks thereafter; and oral administration of 15 mg of the immunomodulator, e.g., methotrexate, weekly.

In one embodiment, the method comprises administering an effective amount of the triple combination therapy to a patient. If the triple combination therapy, or any component of the triple combination therapy, is in a formulation which is in a solid, e.g., dry state, the process of administration can comprise a step of converting the formulation to a liquid state. In one aspect, a dry formulation can be reconstituted, e.g., by a liquid as described above, for use in injection, e.g. intravenous, intramuscular or subcutaneous injection. In another aspect, a solid or dry formulation can be administered topically, e.g., in a patch, cream, aerosol or suppository.

In one embodiment, the present invention provides a method for treating a high risk CD patient with triple combination therapy. The method comprises the steps of administering an initial 300 mg dose of an anti-integrin to a high risk CD patient, administering a subsequent anti-integrin 300 mg dose two weeks after the initial dose, administering a second subsequent anti-integrin 300 mg dose six weeks after the initial dose, and subsequent 300 mg doses every eight weeks thereafter, administering an initial 160 mg dose of a TNF antagonist, followed by a subsequent 80 mg dose of TNF antagonist two weeks after the initial dose, and subsequent 40 mg doses of TNF antagonist every two weeks thereafter, and administering a 15 mg methotrexate dose weekly beginning at Week 0.

The invention provides a triple combination therapy for use in treating an inflammatory bowel disease, such as CD or UC, in a patient having high risk of complications related to the inflammatory bowel disease, such as CD or UC, the use comprising administering an initial dose of anti-integrin, two weeks after the initial dose, and six weeks after the initial dose, and every eight weeks thereafter for a total of 102 weeks; administering an initial dose of TNF antagonist, half the initial dose two weeks after the initial dose, and a quarter of the initial dose every two weeks thereafter for a total of 26 weeks; and administering a weekly dose of an immunomodulator for 34 weeks. In some embodiments, the anti-integrin is vedolizumab. In some embodiments the TNF modulator is adalimumab. In some embodiments the immunomodulator is methotrexate. In some embodiments the triple combination therapy includes administration of vedolizumab, adalimumab, and methotrexate. In some embodiments the triple combination therapy includes vedolizumab, a TNF antagonist, and methotrexate. In some embodiments the triple combination therapy includes vedolizumab, a TNF antagonist, and an immunomodulator. In some embodiments the triple combination therapy includes an anti-α4β7 antibody, a TNF antagonist, and methotrexate.

In one embodiment, the dosing regimen comprises administration of 300 mg of vedolizumab by intravenous infusion at Weeks 0, 2, 6, and then every 8 weeks thereafter; administration of 160 mg of adalimumab by subcutaneous injection at Week 0, administration of 80 mg of adalimumab at Week 2, and then 40 mg of the adalimumab every 2 weeks thereafter; and oral administration of 15 mg of methotrexate weekly.

In some embodiments, the IBD, e.g., CD, has an exacerbation after 26 weeks, e.g., as defined by a CDAI increase of >70 from the prior visit on two occasions two weeks apart and disease activity as seen by colonoscopy and a CRP value above normal (>5 mg/L); or fecal calprotectin >250 µg/g. In an embodiment of exacerbation of IBD, 300 mg vedolizumab may be administered every 4 weeks.

The triple combination therapy may further comprise a corticosteroid tapering regimen, such as beginning about 1 to 3 weeks or about two weeks after starting triple combination therapy. In some embodiments, a high risk IBD patient may be undergoing prior therapy with corticosteroids, such as prednisone, e.g. 10 to 20 mg/day, 20 to 40 mg/day, 25 to 35 mg/day or about 30 mg/day, or budesonide, e.g., 2 to 12 mg/day, 3 to 10 mg/day or about 9 mg/day, at diagnosis or at Baseline. For prednisone, the dose may be reduced at a rate of 5 mg/week until 5 mg/day is reached, then the dose of prednisone is reduced at a rate of 2.5 mg/week until discontinuation. For budesonide, the dose is reduced at a rate of 3 mg every 2 weeks until discontinuation.

In some embodiments, the triple combination therapy of a high risk patient results in endoscopic remission of the inflammatory bowel disease. "Endoscopic remission" as used herein, refers to a condition with a low endoscopic score. An example of a method to assess the endoscopic score in ulcerative colitis is flexible sigmoidoscopy. The endoscopic score in ulcerative colitis can be the Mayo subscore. An example of a method to assess the endoscopic score in Crohn's disease is ileocolonoscopy. The endoscopic score in Crohn's disease can be the simple endoscopic score for Crohn's Disease (SES-CD). The SES-CD can include measures such as the size of ulcers, the amount of ulcerated surface, the amount of affected surface and whether and to what extent the alimentary canal is narrowed.

In an embodiment, a high risk Crohn's disease triple combination therapy patient achieves endoscopic remission as defined by a SES-CD score of 0 to 2 by week 26, or by weeks 22 to 30 or weeks 24 to 28 of treatment. In other embodiments, the triple combination therapy of the invention results in a degree of response or remission selected from the group consisting of SES-CD≤4 and reduction from baseline SES-CD of at least 2 points and no individual SES-CD subscore >1 at Week 26; 50% reduction in SES-CD from Baseline at week 26; deep remission (defined as CDAI<150 and SES-CD 0-2) at week 26; clinical remission (defined as CDAI<150) and endoscopic response as a measure of mucosal healing (defined as 50% reduction in SES-CD from Baseline) at week 26; clinical remission (CDAI score <150) at Weeks 10 and 26; clinical response (defined as ≥100-point decrease in CDAI score) at Weeks 10 and 26; clinical remission (defined as CDAI<150) and C-reactive protein (CRP)<5 mg/L (in subjects with elevated CRP at Baseline) at Weeks 26, 52, 78, and 102; and discontinuation of Baseline corticosteroid use and clinical remission (CDAI score <150) at Weeks 10, 26, and 102.

In some embodiments, a high risk Crohn's disease triple combination therapy patient achieves long-term benefit. In one embodiment, the triple combination therapy of the invention results in maintaining clinical remission (defined as CDAI<150) at Weeks 52, 78, and 102. In another embodiment, the triple combination therapy of the invention results in maintaining endoscopic remission defined as SES-CD 0-2 at Week 102. In another embodiment, the triple combination therapy of the invention results in maintaining deep remission (defined as CDAI<150 and SES-CD 0-2) at Week 102. In other embodiments, the triple combination therapy of the invention results in a degree of long term benefit selected from the group consisting of maintaining endoscopic healing defined as SES-CD≤4 and reduction from baseline SES-CD of at least 2 points and no individual SES-CD subscore >1 at Week 102; maintaining endoscopic response defined as 50% reduction in SES-CD from Baseline at Week 102; maintaining clinical remission (defined as CDAI<150) and endoscopic response as a measure of mucosal healing (defined as 50% reduction in SES-CD from baseline) at Week 102; achieving normalization of CRP defined as <5 mg/L at Week 26 (in those elevated at Baseline); and achieving a Patient-reported outcome 2 (PRO-2) score ≤75 (a subset of the CDAI score and derived from a combination of liquid or very soft stools (multiplied by 2) and abdominal pain severity ((on a scale of 0 to 3) multiplied by 5) over averaged over the prior 7 days) and an SES-CD≤4 and a reduction from baseline SES-CD of at least 2 points and no individual SES-CD subscore >1 at Weeks 26 and 102.

High Risk Crohn's Disease Patients

In one embodiment, the triple combination therapy disclosed herein is used to treat a subpopulation of Crohn's disease patients who are at risk for developing complications following diagnosis. Such high risk patients may be identified using predictive methods known in the art, including, for example, the PROSPECT predictive method. As described in Siegel et al. (2016) *Aliment Pharmacol Ther* 43: 262-271, the PROSPECT predictive test is based on clinical, serologic and genetic variables of the patient, and is used to determine the likelihood that a CD patient will have a disease complication by year 2 of diagnosis. A high risk CD patient is one who has at least a 20% chance of such a complication by year 2, as determined by, for example, the PROSPECT predictive method.

High Risk Ulcerative Colitis Disease Patients

In one embodiment, the triple combination therapy disclosed herein is used to treat a subpopulation of UC disease patients who are at risk for developing complications following diagnosis. Such high risk UC patients are understood to be at an increased risk for colectomy. High risk UC patents may also be identified by their failure to maintain steroid-induced remission.

The invention will be more fully understood by reference to the following examples. They should not, however, be construed as limiting the scope of the invention. All literature and patent citations are incorporated herein by reference.

EXEMPLIFICATION

Example 1

A phase 4, open-label, multicenter study in subjects with newly-diagnosed CD at higher risk for complications due to aggressive disease is designed to evaluate the safety, tolerability, and clinical activity of triple combination therapy (300 mg vedolizumab IV, 160/80/40 mg adalimumab SC, and 15 mg oral methotrexate). A predictive tool incorporating clinical, serological, and genetic variables will be used to stratify which subjects are at higher risk for developing complications. The study will run over a 26-week treatment period for induction of endoscopic remission and mucosal healing followed by efficacy and safety of vedolizumab IV monotherapy to maintain remission for 76 weeks, for a total treatment period of 102 weeks.

Patients are eligible for the study if they have been diagnosed with CD within the previous 18 months, and are naïve to biologics. Patients who meet all eligibility criteria and provide written informed consent are enrolled in this study.

Patients are excluded from the study if they are at low risk for CD complications as calculated by the CD PROSPECT predictive tool, have any evidence of active infection during screening, have a history of any bacterial, viral, and other infection due to opportunistic pathogens, have had any prior exposure to any TNF antagonist biologic therapy, or to vedolizumab, natalizumab, efalizumab, or rituximab, have any prior CD-related surgery or CD complication requiring surgery, have a history of tuberculosis, lymphoma, lymphoproliferative disease, or congestive heart failure or unstable angina. Patients with a medical history that contradicts the use of methotrexate or adalimumab or indicates intolerance to methotrexate or adalimumab are also excluded.

The study consists of up to a 4-week screening period, a 26-week combination treatment period, an additional 76-week vedolizumab IV monotherapy treatment period, and a 26-week follow-up period following last dose (with final efficacy evaluations at week 120). The duration of the study from Screening to final efficacy visit at Week 120 will be approximately 124 weeks. All subjects will participate in safety follow-up telephone calls 18 and 26 weeks after last dose, for a total follow-up of 128 weeks. Subjects who discontinue early will also participate in safety follow-up telephone calls 18 and 26 weeks after their last dose. The primary endpoint will be subjects achieving endoscopic remission (defined as Simple Endoscopic Score for Crohn's Disease (SES-CD) 0-2) at Week 26. The SES-CD evaluates 4 endoscopic variables (ulcer size, proportion of the surface area that is ulcerated, proportion of the surface area affected, and stenosis) by scoring each variable on a scale from 0 to 3 where higher scores indicate more severe disease, in 5 colonic segments (ileum, right colon, transverse colon, left colon, and rectum). The score for each endoscopic variable is the sum of the values obtained for each segment. The SES-CD Total is the sum of the 4 endoscopic variable scores from 0 to 56.

Vital signs, physical and neurological examinations, adverse event (AE) assessments, and laboratory values (chemistry, hematology, and urinalysis) are obtained to evaluate the safety and tolerability of the triple combination therapy. To exclude patients with progressive multifocal leukoencephalopathy (PML), a Risk Assessment and Minimization for PML (RAMP) questionnaire is administered at Screening and prior to dosing at each visit, to evaluate symptoms suggestive of PML.

The invention claimed is:

1. A method of treating Crohn's Disease (CD) in a patient, wherein the method comprises the step of:
   administering to a human patient identified as a high-risk CD patient, a triple combination therapy comprising a humanized anti-α4β7 antibody, adalimumab, and methotrexate,
   wherein the triple combination therapy is administered to the patient according to the following dosing regimen:
   a. an initial dose of 155 to 180 mg of humanized anti-α4β7 antibody as an intravenous infusion, followed by a second subsequent dose of 155 to 180 mg of humanized anti-α4β7 antibody as an intravenous infusion at about two weeks after the initial dose; followed by a third subsequent dose of 155 to 180 mg of the humanized anti-α4β7 antibody as an intravenous infusion at about six weeks after the initial dose;
   b. an initial dose of 160 mg of adalimumab as a subcutaneous injection, followed by a second subsequent dose of 80 mg of adalimumab as a subcutaneous injection, followed by a third subsequent dose of 40 mg of adalimumab at about four weeks after the initial dose; and
   c. an initial dose of 15 mg of methotrexate;
   further wherein the anti-α4β7 antibody comprises an antigen binding region of nonhuman origin and at least a portion of an antibody of human origin, wherein the humanized antibody has binding specificity for the α4β7 complex, wherein the antigen-binding region comprises the CDRs:
   Light chain:
   CDR1 SEQ ID NO:7
   CDR2 SEQ ID NO:8 and
   CDR3 SEQ ID NO:9; and
   Heavy chain:
   CDR1 SEQ ID NO:4
   CDR2 SEQ ID NO:5 and
   CDR3 SEQ ID NO:6.

2. The method of claim 1, wherein the humanized anti-α4β7 antibody has a heavy chain variable region sequence of amino acids 20 to 140 of SEQ ID NO: 1 and/or a light chain variable region sequence of amino acids 20 to 131 of SEQ ID NO:2.

3. The method of claim 1, wherein the humanized anti-α4β7 antibody has a heavy chain comprising amino acids 20 to 470 of SEQ ID NO:1 and a light chain comprising amino acids 20 to 238 of SEQ ID NO:2.

4. The method of claim 1, wherein the anti-α4β7 antibody is vedolizumab.

5. The method of claim 1, wherein the high-risk CD patient additionally is administered a dose of corticosteroid.

6. A method of treating Crohn's Disease in a patient, comprising administering to the patient vedolizumab, adalimumab, and methotrexate according to a triple combination therapy, wherein the triple combination therapy comprises
   administering vedolizumab at a dose of 155 to 180 mg at weeks 0, 2, and 6, followed by administration every 8 weeks thereafter;
   subcutaneously administering a 160 mg dose of adalimumab at week 0, an 80 mg dose of adalimumab at week 2, and a 40 mg dose of adalimumab at week 4 and every two weeks thereafter; and
   administering 15 mg methotrexate;
   wherein the patient is at high risk of complication from the Crohn's disease.

7. The method of claim 6, wherein adalimumab is discontinued at week 26.

8. The method of claim 6, wherein the methotrexate is administered orally.

9. The method of claim 6, wherein the methotrexate is discontinued at week 34.

10. The method of claim 6, wherein the patient is a high-risk Crohn's disease patient.

11. A method of treating Crohn's Disease in a patient, comprising administering to the patient vedolizumab, infliximab, and methotrexate according to a triple combination therapy, wherein the triple combination therapy comprises
    administering vedolizumab at a dose of 155 to 180 mg at weeks 0, 2, and 6, followed by administration every 8 weeks thereafter;
    intravenously administering infliximab at a dose of 5 mg/kg at weeks 0, 2 and 6, and then every 8 weeks thereafter; and
    administering 15 mg methotrexate;
    wherein the patient is at high risk of complication from the Crohn's disease.

12. The method of claim 11, wherein infliximab is discontinued at week 26.

13. The method of claim 11, wherein the methotrexate is administered orally.

14. The method of claim 11, wherein the methotrexate is discontinued at week 34.

15. The method of claim 11, wherein vedolizumab is administered at a dose of 155 to 170 mg.

* * * * *

```
                              SEQUENCE LISTING

<160> NUMBER OF SEQ ID NOS: 11

<210> SEQ ID NO 1
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Gly Ser Gly Tyr Thr Phe
            35                  40                  45

Thr Ser Tyr Trp Met His Trp Val Arg Gln Ala Pro Gly Gln Arg Leu
        50                  55                  60

Glu Trp Ile Gly Glu Ile Asp Pro Ser Glu Ser Asn Thr Asn Tyr Asn
65                  70                  75                  80

Gln Lys Phe Lys Gly Arg Val Thr Leu Thr Val Asp Ile Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255
```

```
Leu Ala Gly Ala Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 2
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Pro Gly Glu Pro Ala Ser Ile Ser Cys Arg Ser Ser Gln Ser Leu
            35                  40                  45

Ala Lys Ser Tyr Gly Asn Thr Tyr Leu Ser Trp Tyr Leu Gln Lys Pro
50                  55                  60

Gly Gln Ser Pro Gln Leu Leu Ile Tyr Gly Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Leu Gln Gly Thr His Gln Pro Tyr Thr Phe Gly Gln Gly Thr Lys Val
            115                 120                 125
```

```
Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235
```

<210> SEQ ID NO 3
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

Arg Ala Asp Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

<210> SEQ ID NO 4
<211> LENGTH: 5
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Tyr Trp Met His
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Ile Asp Pro Ser Glu Ser Asn Thr Asn Tyr Asn Gln Lys Phe Lys
1               5                   10                  15

Gly

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Tyr Asp Gly Trp Asp Tyr Ala Ile Asp Tyr
1               5                   10

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ser Ser Gln Ser Leu Ala Lys Ser Tyr Gly Asn Thr Tyr Leu Ser
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Ile Ser Asn Arg Phe Ser
1               5

<210> SEQ ID NO 9
<211> LENGTH: 9
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 9

Leu Gln Gly Thr His Gln Pro Tyr Thr
1               5

<210> SEQ ID NO 10
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Lys Val Glu Ile Lys
            100                 105                 110

<210> SEQ ID NO 11
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
            115